US012575908B2

(12) United States Patent (10) Patent No.: US 12,575,908 B2

Dal Pont (45) Date of Patent: Mar. 17, 2026

(54) SURGICAL MICROSCOPE

(71) Applicant: Dal Pont Medical S.r.l.s., Treviso (IT)

(72) Inventor: Franco Dal Pont, Treviso (IT)

(73) Assignee: Dal Pont Medical S.r.l.s., Treviso (IT)

( * ) Notice: Subject to any disclaimer, the term of this patent is extended or adjusted under 35 U.S.C. 154(b) by 366 days.

(21) Appl. No.: 18/028,790

(22) PCT Filed: Sep. 14, 2021

(86) PCT No.: PCT/IT2021/050281
§ 371 (c)(1),
(2) Date: Mar. 28, 2023

(87) PCT Pub. No.: WO2022/064536
PCT Pub. Date: Mar. 31, 2022

(65) Prior Publication Data

US 2023/0329825 A1 Oct. 19, 2023

(30) Foreign Application Priority Data

Sep. 28, 2020 (IT) ........................ 102020000022843

(51) Int. Cl.
*A61B 90/25* (2016.01)
*A61B 90/50* (2016.01)

(52) U.S. Cl.
CPC .............. *A61B 90/25* (2016.02); *A61B 90/50* (2016.02); *A61B 2090/504* (2016.02)

(58) Field of Classification Search
CPC ................................. A61B 90/25; A61B 90/50
USPC ......................................................... 359/368
See application file for complete search history.

(56) References Cited

U.S. PATENT DOCUMENTS

| | | | | |
|---|---|---|---|---|
| 4,515,333 | A | 5/1985 | Pugh et al. | |
| 5,173,802 | A | 12/1992 | Heller | |
| 5,552,929 | A * | 9/1996 | Fukaya | H04N 13/239 |
| | | | | 348/E13.064 |
| 8,416,492 | B2 | 4/2013 | Enge | |
| 2003/0151806 | A1* | 8/2003 | Schmidt | A61B 90/25 |
| | | | | 359/368 |
| 2004/0113029 | A1* | 6/2004 | Piontkowski | F16M 11/14 |
| | | | | 248/123.11 |
| 2005/0228257 | A1* | 10/2005 | Ishikawa | A61B 90/25 |
| | | | | 600/407 |

OTHER PUBLICATIONS

International Search Report and the Written Opinion Dated Dec. 22, 2021 From the International Searching Authority Re. Application No. PCT/IT2021/050281. (12 Pages).
Rapporto di Ricerca e l'Opinione Scritta [Search Report and the Written Opinion] Dated Jun. 23, 2021 From the Ministero Dello Sviluppo Economico, Direzione Generale Sviluppo Produttivo e Competitivita, Ufficio Italiano Brevetti e Marchi Re. Application No. IT 202000022843. (9 Pages).

\* cited by examiner

*Primary Examiner* — Sharrief I Broome

(57) ABSTRACT

A surgical microscope having an optical body connected to a holder by a hinge, and a balancing device. The device includes a counterweight, connected in at least one connection point to the optical body of the surgical microscope through a support which allows the free rotation of the counterweight around the connection point so as to balance the weight distribution of the optical body (with respect to the hinge and prevent unwanted rotations of the optical body.

3 Claims, 1 Drawing Sheet

SURGICAL MICROSCOPE

RELATED APPLICATIONS

This application is a National Phase of PCT Patent Application No. PCT/IT2021/050281 having International filing date of Sep. 14, 2021, which claims the benefit of priority of Italy Patent Application No. 102020000022843 filed on Sep. 28, 2020. The contents of the above applications are all incorporated by reference as if fully set forth herein in their entirety.

FIELD AND BACKGROUND OF THE INVENTION

This invention relates to a surgical microscope.

In particular, the invention relates to a surgical microscope equipped with a balancing device and used to perform precision surgical operations, for example, in the field of otolaryngology, neurosurgery, or dentistry.

In these areas, it is necessary to put the surgeon in such conditions so that he can complete the operation in the best possible way for the patient.

It is therefore necessary to arrange highly performing instrumentation, including the surgical microscope, which does not hinder or slow down the surgeon's work, but which on the contrary, facilitates him as much as possible.

Currently known surgical microscopes generally comprise an optical body hinged to a frame consisting of articulated arms.

The optical body houses all the components used for enlargement, lighting and also the possible transmission of digital images.

In addition, it is equipped with grips or handles through which the surgeon can modify its position and orientation within the operating field according to needs.

Since the direction of the resulting force acting on the centre of gravity of the optical body is normally never aligned with the connection point to the frame, a moment is consequently created which induces an unwanted rotation of the optical body itself.

The possible approaches usually adopted by manufacturers to overcome this drawback are to:

calibrate the microscopes at the end of the production process so that they are already balanced. However, this makes it impossible to install additional accessories (such as eyepieces, optical distributors, video acquisition systems, etc.) not foreseen in the design phase, as they would alter the distribution of the masses and cause the optical body to rotate again;

equip the optical body with Cartesian micrometric slides that can be adjusted by means of special knobs, with which the surgeon can vary the position of the centre of gravity in order to cancel the acting moment, but delaying the execution of the operation and increasing the risk of making mistakes;

install compensation systems, for example springs or other elastic means, capable of opposing the moment generated on the centre of gravity, but which cause a certain encumbrance.

Such systems have other drawbacks in addition to those described up to now, such as poor ease of use, low manoeuvrability, and they are also expensive and complicated to design and install.

SUMMARY OF THE INVENTION

The object of this invention is to provide a surgical microscope equipped with a balancing device which solves the aforementioned drawbacks, including poor and difficult manoeuvrability.

A further object of the invention is to provide a surgical microscope equipped with a balancing device which allows any accessory instrumentation to be connected to the optical body, without thereby losing the balance.

Another object of the invention is to provide a surgical microscope equipped with a balancing device which is simple and economical to install and use, in place of the advantages obtained.

This and other aims are achieved by a surgical microscope according to the attached independent claim.

Further detailed features and advantages of the invention are contained in the subsequent dependent claims.

BRIEF DESCRIPTION OF THE SEVERAL VIEWS OF THE DRAWINGS

The invention will now be described by way of non-limiting example according to some of its preferred embodiments, with the aid of the attached drawings, in which.

DESCRIPTION OF SPECIFIC EMBODIMENTS OF THE INVENTION

Figure 1:
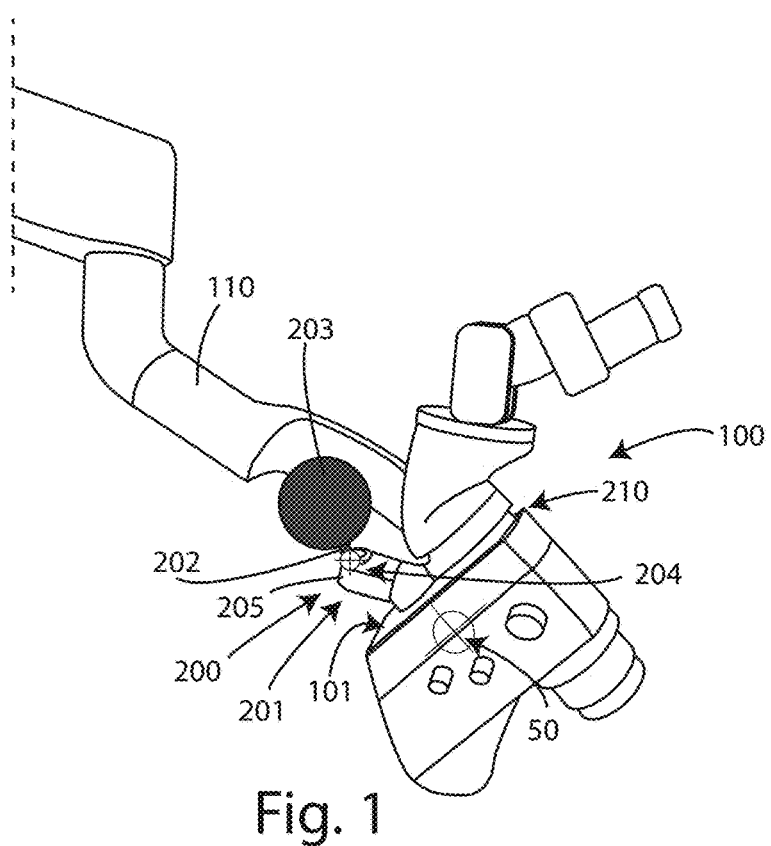
FIG. 1 is a schematic view of a surgical microscope equipped with a first embodiment of the balancing device according to this invention.
Figure 2:
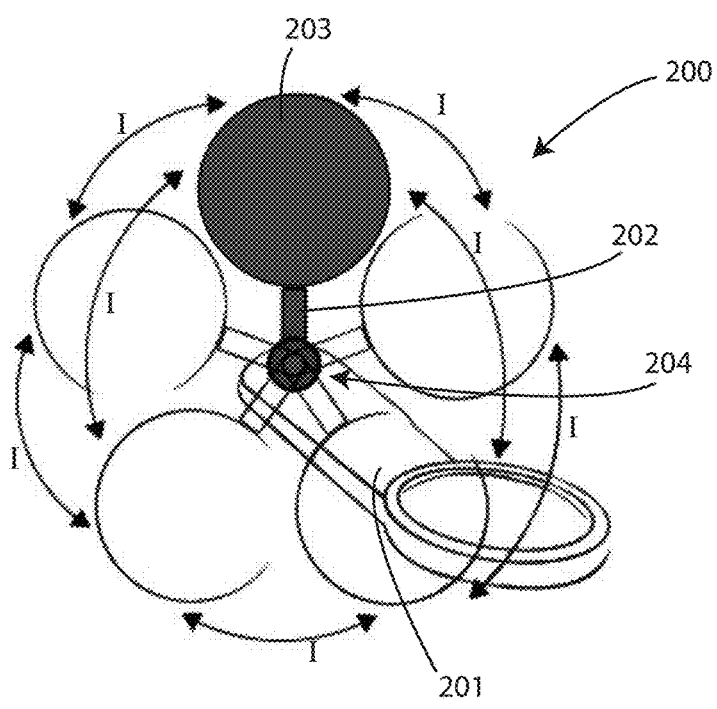
FIG. 2 is a schematic perspective representation of a second embodiment of the balancing device for a surgical microscope according to this invention.

With reference to FIGS. 1 and 2, an optical assembly 100 of a surgical microscope is schematically represented, connected by means of a hinge 50 to an arm 110 of a support frame.

The optical body 100 of the surgical microscope is free to rotate around the hinge 50, and this causes numerous drawbacks during the operating procedures, as will be explained in detail below.

The balancing device 200 according to the invention is positioned at a wall 101 of the optical body 100, preferably the upper one.

This device comprises a support 201 fixed to the optical body 100 and a counterweight 203 connected to it.

In a preferred embodiment, the support 201 has an annular portion 210 to be interposed between the eyepieces of the microscope and the lower body, to which the eyepieces are removably connected.

In this way, the balancing device according to the invention can be installed on different and already existing microscopes simply by varying the dimensions of the annular portion 210 of the support 201.

The counterweight 203 has a rod or arm 202 equipped with a connection 204 of the "ball head" type; the support 201 consequently comprises a threaded ring 205 which limits or allows the movement of the head in the respective seat according to the clamping force applied.

Alternative clamping methods to the threaded ring 205 may be present in other preferred embodiments, such as adjustment pins or knobs, all having the same effect of locking the counterweight 203 in a determined position.

FIG. 2 shows a constructive detail of the device according to the invention, in an operating situation.

In conventional systems, if the surgeon makes even minimal inclination movements of the eyepiece body of the microscope, the centre of gravity is displaced, and this generates a rotation of the entire optical body.

The eyepiece body is generally tiltable within a 90 degree angle so it can be positioned in a variable direction with respect to the optical body itself, shifting the centre of gravity of the entire microscope.

The device according to the invention advantageously allows fine balancing adjustments to be made, even during operating procedures.

Currently, this slight imbalance is compensated for by slightly tightening the couplings placed on the joints, but effectively immobilizing the microscope in its position.

This would also have the effect of delaying the operation, and could also increase the chances of error in its execution as the surgeon must necessarily divert attention from the operating field to adjust the position of the microscope.

The adjustment device according to the invention advantageously allows maintaining the centre of gravity of the optical body 100 in proximity of the hinge 50 by simple rotations of the counterweight 203 around the connection 204.

In this way, the creation of a mechanical moment and also the consequent rotation of the body 100 itself is avoided.

Operationally, the surgeon, after loosening the threaded ring 205, moves the counterweight 203 in a direction indicated by the arrows I, to then lock it once the balance has been reached.

At this point, the surgeon will be able to make all the movements he deems necessary, within an interval of space that reasonably extends at least over the entire operating field, without the fear of having to continuously adjust the position of the optical body 100 at every minimum movement.

The invention described may be modified and adapted in several ways without thereby departing from the scope of the inventive concept.

Further, all the details can be replaced by other technically-equivalent elements.

Lastly, the components used, providing they are compatible with the specific use, as well as the dimensions, may vary according to requirements and the state of the art.

Where the features and the techniques mentioned in the following claims are followed by reference signs, the reference signs have been used only with the aim of increasing the intelligibility of the claims themselves and, consequently, the reference signs do not constitute in any way a limitation to the interpretation of each element identified, purely by way of example, by the reference signs.

The invention claimed is:

1. A surgical microscope comprising
an optical body connected to a holder by a hinge, and
a balancing device,
wherein said optical body comprises eyepieces of said microscope and a lower body and wherein said microscope also comprises
a counterweight, connected in at least one connection point to said optical body of said microscope by a support fixed to said optical body,
wherein the support allows the free rotation of said counterweight around the at least one connection point for adjusting a position of said counterweight relative to said optical body, so as to balance the weight distribution of said optical body with respect to said hinge through said adjustment of said counterweight position, and thereby prevent unwanted rotation of said optical body,
wherein said support includes a fastening annular portion that forms an attachment interface configured to be interposed between said eyepieces of the microscope and said lower body
to said optical body through said annular portion of said support that is part of said balancing device.

2. The surgical microscope according to claim 1, wherein said
connection point which connects said counterweight to said support is of the "ball head" type.

3. The surgical microscope according to claim 1, wherein the
counterweight is connected to said support at said connection point by an arm and a threaded ring attached to said support.

* * * * *